United States Patent
Stevens et al.

(10) Patent No.: US 6,502,574 B2
(45) Date of Patent: Jan. 7, 2003

(54) LATERAL STIFFENING SNORING TREATMENT

(75) Inventors: Walter J. Stevens, Woodbury, MN (US); Anja K. Metzger, Stillwater, MN (US); Larry A. Walter, Minneapolis, MN (US); Mark B. Knudson, Shoreview, MN (US); Timothy R. Conrad, Eden Prairie, MN (US)

(73) Assignee: Pi Medical, Inc., St. Paul, MN (US)

( * ) Notice: Subject to any disclaimer, the term of this patent is extended or adjusted under 35 U.S.C. 154(b) by 0 days.

(21) Appl. No.: 09/992,277

(22) Filed: Nov. 14, 2001

(65) Prior Publication Data

US 2002/0035994 A1 Mar. 28, 2002

Related U.S. Application Data (63) Continuation-in-part of application No. 09/814,460, filed on Mar. 21, 2001, which is a continuation-in-part of application No. 09/602,141, filed on Jun. 23, 2000, which is a continuation-in-part of application No. 09/513,432, filed on Feb. 25, 2000, and a continuation-in-part of application No. 09/513,039, filed on Feb. 25, 2000, which is a continuation-in-part of application No. 09/434,653, filed on Nov. 5, 1999, which is a continuation-in-part of application No. 09/398,991, filed on Sep. 17, 1999, now Pat. No. 6,250,307, and a continuation-in-part of application No. 09/636,803, filed on Aug. 10, 2000.

(51) Int. Cl.[7] ................................................. A61F 5/56
(52) U.S. Cl. ........................................ 128/848; 602/902
(58) Field of Search ..................... 128/846, 848, 128/859–862; 602/902

(56) References Cited

U.S. PATENT DOCUMENTS 3,132,647 A * 5/1964 Corniello .................... 128/848
3,998,209 A 12/1976 Macvaugh (List continued on next page.)

FOREIGN PATENT DOCUMENTS

| DE | 200 15 980 U1 | 3/2001 |
| EP | 0264516 * | 4/1988 |
| EP | 0 706 808 A1 | 4/1996 |
| SU | 1553140 | 3/1990 |
| WO | WO 99/33414 | 7/1999 |
| WO | WO 01/19301 | 3/2001 |
| WO | WO 01/23039 | 4/2001 |

OTHER PUBLICATIONS

Lemperle, G. et al., "PMMA Microspheres (Artecoll) for Skin and Soft–Tissue Augmentation. Part II: Clinical Investigations", *Plast. Reconstr. Surg.*, vol. 96, pp. 627–634 (Sep. 1995).

(List continued on next page.)

*Primary Examiner*—Michael A. Brown
(74) *Attorney, Agent, or Firm*—Merchant & Gould P.C.

(57) ABSTRACT

A method for treating snoring includes identifying first and second locations disposed on right and left sides, respectively, of a soft palate and separated by an anterior-posterior midline extending centrally positioned on the palate. The first and second locations are linked across the midline by creating a linkage between the first and second locations and through the midline with the linkage having a stiffness greater than a stiffness of untreated tissue naturally residing between the locations.

20 Claims, 9 Drawing Sheets

U.S. PATENT DOCUMENTS

| | | | |
|---|---|---|---|
| 4,669,459 A | * 6/1987 | Spiewak | 128/848 |
| 4,830,008 A | 5/1989 | Meer | |
| 4,978,323 A | 12/1990 | Freedman | |
| 5,046,512 A | 9/1991 | Murchie | |
| 5,052,409 A | 10/1991 | Tepper | |
| 5,133,354 A | 7/1992 | Kallok | |
| 5,176,618 A | 1/1993 | Freedman | |
| 5,178,156 A | 1/1993 | Takishima et al. | |
| 5,190,053 A | 3/1993 | Meer | |
| 5,281,219 A | 1/1994 | Kallok | |
| 5,284,161 A | 2/1994 | Karell | |
| 5,421,406 A | 6/1995 | Furusawa et al. | |
| 5,451,406 A | 9/1995 | Lawin et al. | |
| 5,456,662 A | 10/1995 | Edwards et al. | |
| 5,514,131 A | 5/1996 | Edwards et al. | |
| 5,540,733 A | 7/1996 | Testerman et al. | |
| 5,582,184 A | 12/1996 | Erickson et al. | |
| 5,591,216 A | 1/1997 | Testerman et al. | |
| 5,630,833 A | 5/1997 | Katsaros et al. | |
| 5,674,191 A | 10/1997 | Edwards et al. | |
| 5,718,702 A | 2/1998 | Edwards | |
| 5,792,067 A | 8/1998 | Karell | |
| 5,792,478 A | 8/1998 | Lawin et al. | |
| 5,843,021 A | 12/1998 | Edwards et al. | |
| RE36,120 E | 3/1999 | Karell | |
| 5,897,579 A | 4/1999 | Sanders | |
| 5,915,385 A | * 6/1999 | Hakimi | 128/859 |
| 5,922,006 A | 7/1999 | Sugerman | |
| 5,983,136 A | 11/1999 | Kamen | |
| 5,988,171 A | 11/1999 | Sohn et al. | |
| 6,098,629 A | 8/2000 | Johnson et al. | |
| 6,250,307 B1 | 6/2001 | Conrad et al. | |

OTHER PUBLICATIONS

Boot, H. et al., "Long–Term Results of Uvulopalatopharyngoplasty for Obstructive Sleep Apnea Syndrome", The Laryngoscope, pp. 469?475 (Mar. 2000).

Boudewyns et al., "Temperature controlled Radiofrequency Tissue Volume Reduction of the Soft Palate (Somnoplasty®) in the Treatment of Habitual Snoring: Results of a European Multicenter Trial", Acta Otolaryngol, vol. 120 pp. 981 985 (2000).

Brietzke et al., "Injection Snoreplasty: How to Treat Snoring Without All the Pain and Expense", Otolaryngology Head and Neck Surgery, pp. 503–510 (May 2001).

Brochure, "Our Diagnostic Procedures are a Snap®!", Snap Laboratories, 4 pgs.

Brochure, "Snore–Free Nights—Guaranteed!", Your Health News, 2 pgs.

Brochure, "Snoreless™", Nutrition for Life International, 2 pgs. (Dec. 1999).

Brochure, "Haven't you suffered from Snoring long enough", SomnoplastySM, 2 pgs.

Cole, P. et al., "Snoring: A Review and a Reassessment", The Journal of Otolaryngology, vol. 24, No. 5, pp. 303–306 (1995).

Coleman, S. et al., "Midline Radiofrequency Tissue Reduction of the Palate for Bothersome Snoring and Sleep–Disordered Breathing: A Clinical Trial", Otolaryngology–Head and Neck Surgery, pp. 387–394 (Mar. 2000).

Courey, et al., "Histologic and Physiologic Effects of Electrocautery, CO2 Laser, and Radiofrequency Injury in the Porcine Soft Palate", Laryngoscope, vol. 109, pp. 1316–1319 (Aug. 1999).

Dalmasso, F. et al., "Snoring: analysis, measurement, clinical implications and applications", Eur. Respir. J., vol. 9, pp. 146–159 (1996).

Du, G. et al., "Geometric Modeling of 3–D Braided Preforms for Composites", Textile Structural Composites Symposium, Drexel University, Philadelphia, Pennsylvania, 25 pages, (1991).

Ellis, P. D. M. et al., "Surgical relief of snoring due to palatal flutter: a preliminary report", Annals of the Royal College of Surgeons of England, vol. 75, No. 4, pp. 286–290 (1993).

Fischer, Y. et al., "Die Radiofrequenzablation des weichen Gaumens (Somnoplastik)", Redaktion, pp. 33–40 (2000).

Gillette, P. et al., "Pediatric Cardiac Pacing", Cardiology Clinics, vol. 10, No. 4, pp. 749–754 (Nov. 1992).

Harries, P.G. et al., "Review Article: The surgical treatment of snoring", The Journal of Laryngology and Otology, vol. 110, pp. 1105–1106 (Dec. 1996).

Huang, L. et al., "Biomechanics of snoring", Endeavour, vol. 19, No. 3, pp. 96–100 (1995).

Huang, L., "Flutter of Cantilevered Plates in Axial Flow", Journal of Fluids and Structures, vol. 9, pp. 127–147 (1995).

Hukins et al., "Radiofrequency Tissue Volume Reduction of the Soft Palate in Simple Snoring", Arch. Otolaryngol Head Neck Surg, vol. 126, pp. 602–606 (2000).

Kasey, K. et al., "Radiofrequency Volumetric Reduction of the Palate: An Extended Follow–Up Study", Otolaryngology–Head and Neck Surgery, vol. 122, No. 3, pp. 410–414 (Mar. 2000).

Ko, F., "Braiding", Engineered Materials Handbook, vol. 1, Composites, T.J. Reinhart, Editor, ASM International, Metals Park, Ohio 44073, pp. 519–528 (1987).

LaFrentz et al., "Palatal Stiffening Techniques for Snoring in a Novel Canine Model", Abstracts of the Twenty–Second Annual MidWinter Meeting of the Association for Research in Otolaryngology, Abstract No. 499, vol. 22, pp. 125–126 (Feb. 13–18, 1999).

Littlefield, et al., "Snoring Surgery: Which One Is Best for You?", ENT –Ear, Nose & Throat Journal, vol. 78, No. 11, pp. 861–870 (Nov. 1999).

C. Lorenz, "If he Snores—what can you do about it?", Today's Woman, Jul. 1948, p. 112.

Mair et al., "Cautery–Assisted Palatal Stiffening Operation", Otolaryngology Head and Neck Surgery, vol. 122, No. 4, pp. 547–555 (Apr. 2000).

Schwartz, R.S. et al., "Effects of electrical stimulation to the soft palate on snoring and obstructive sleep apnea", J. Prosthet. Dent., vol. 76, No. 3, pp. 273–281 (1996).

Wiltfang, J. et al., "First results on daytime submadibular electrostimulation of suprahyoidal muscles to prevent night-–time hypopharyngeal collapse in obstructive sleep apnea syndrome", Int. J. Oral Maxillofac. Surg., vol. 28, pp. 21–25 (1999).

* cited by examiner

LATERAL STIFFENING SNORING TREATMENT

CROSS-REFERENCE TO RELATED APPLICATION

The present application is a continuation-in-part of U.S. patent application Ser. No. 09/814,460 filed Mar. 21, 2001 as a continuation-in-part of U.S. patent application Ser. No. 09/602,141 filed Jun. 23, 2000 which is a continuation-in-part of U.S. patent application Ser. No. 09/513,432 and Ser. No. 09/513,039 both filed Feb. 25, 2000, which are continuations-in-part of U.S. patent application Ser. No. 09/434,653 filed on Nov. 5, 1999 which is a continuation-in-part of U.S. patent application Ser. No. 09/398,991 filed Sep. 17, 1999 (now U.S. Pat. No. 6,250,307 issued Jun. 26, 2001), and the present application is a continuation-in-part of U.S. patent application Ser. No. 09/636,803 filed Aug. 10, 2000, with priority being claimed to all of the fore-going.

BACKGROUND

1. Field of the Invention

This invention is directed to a method of treating snoring. More particularly, this invention is directed to such a treatment for linking left and right sides of a patient's palate.

2. Description of the Prior Art

Snoring has received increased scientific and academic attention. One publication estimates that up to 20% of the adult population snores habitually. Huang, et al., "Biomechanics of Snoring", *Endeavour*, p. 96–100, Vol. 19, No. 3 (1995). Snoring can be a serious cause of marital discord. In addition, snoring can present a serious health risk to the snorer. In 10% of habitual snorers, collapse of the airway during sleep can lead to obstructive sleep apnea syndrome. Id.

Notwithstanding numerous efforts to address snoring, effective treatment of snoring has been elusive. Such treatment may include mouth guards or other appliances worn by the snorer during sleep. However, patients find such appliances uncomfortable and frequently discontinue use (presumably adding to marital stress).

Electrical stimulation of the soft palate has been suggested to treat snoring and obstructive sleep apnea. See, e.g., Schwartz, et al., "Effects of electrical stimulation to the soft palate on snoring and obstructive sleep apnea", *J. Prosthetic Dentistry*, pp. 273–281 (1996). Devices to apply such stimulation are described in U.S. Pat. Nos. 5,284,161 and 5,792,067. Such devices are appliances requiring patient adherence to a regimen of use as well as subjecting the patient to discomfort during sleep. Electrical stimulation to treat sleep apnea is discussed in Wiltfang, et al., "First results on daytime submandibular electrostimulation of suprahyoidal muscles to prevent night-time hypopharyngeal collapse in obstructive sleep apnea syndrome", *International Journal of Oral & Maxillofacial Surgery*, pp. 21–25 (1999).

Surgical treatments have been employed. One such treatment is uvulopalatopharyngoplasty. In this procedure, so-called laser ablation is used to remove about 2 cm of the trailing edge of the soft palate thereby reducing the soft palate's ability to flutter between the tongue and the pharyngeal wall of the throat. The procedure is frequently effective to abate snoring but is painful and frequently results in undesirable side effects. Namely, removal of the soft palate trailing edge compromises the soft palate's ability to seal off nasal passages during swallowing and speech. In an estimated 25% of uvulopalatopharyngoplasty patients, fluid escapes from the mouth into the nose while drinking. Huang, et al., supra at 99. Uvulopalatopharyngoplasty (UPPP) is also described in Harries, et al., "The Surgical treatment of snoring", *Journal of Laryngology and Otology*, pp. 1105–1106 (1996) which describes removal of up to 1.5 cm of the soft palate. Assessment of snoring treatment is discussed in Cole, et al., "Snoring: A review and a Reassessment", *Journal of Otolaryngology*, pp. 303–306 (1995).

Huang, et al., supra, describe the soft palate and palatal snoring as an oscillating system which responds to airflow over the soft palate. Resulting flutter of the soft palate (rapidly opening and closing air passages) is a dynamic response generating sounds associated with snoring. Huang, et al., propose an alternative to uvulopalatopharyngoplasty. The proposal includes using a surgical laser to create scar tissue on the surface of the soft palate. The scar is to reduce flexibility of the soft palate to reduce palatal flutter. Huang, et al., report initial results of complete or near-complete reduction in snoring and reduced side effects.

Surgical procedures such as uvulopalatopharyngoplasty and those proposed by Huang, et al., continue to have problems. The area of surgical treatment (i.e., removal of palatal tissue or scarring of palatal tissue) may be more than is necessary to treat the patient's condition. Surgical lasers are expensive. The proposed procedures are painful with drawn out and uncomfortable healing periods. The procedures have complications and side effects and variable efficacy (e.g., Huang, et al., report promising results in 75% of patients suggesting a full quarter of patients are not effectively treated after painful surgery). The procedures may involve lasting discomfort. For example, scar tissue on the soft palate may present a continuing irritant to the patient. Importantly, the procedures are not reversible in the event they happen to induce adverse side effects not justified by the benefits of the surgery.

Commonly assigned U.S. Pat. No. 6,250,307 issued Jun. 26,2001; International application PCT/US00/26616 (International Publication No. WO 01/23039 A1 published Apr. 5, 2001), International application PCT/US00/40830 (International Publication No. No. WO 01/19301 A1 published Mar. 22, 2001), and International application PCT/US01/24255 (International Publication No. WO 02/13738 published Feb. 2, 2001 all teach structure of various designs of implants for treatment of snoring. In addition, snoring treatments include RF ablation of palatal tissue as described and marketed by Somnus Technologies, Inc. (Kasey et al., "Radiofrequency Volumetric Reduction of the Palate: An Extended Follow-Up Study", *Otolaryngology—Head and Neck Surgery*, Vol. 122, No. 3, pp. 410–414 (March 2000)) and use of injected sclerosing agents in the soft palate as taught in LaFrentz et al., "Palatal Stiffening Techniques for Snoring in a Novel Canine Model", *Abstracts of the Twenty-Second Annual MidWinter Meeting of the Association for Research in Otolaryngology*, Abstract NO. 499, Vol. 22, pp. 125–126 (Feb. 13–18, 1999). The Somnus Technologies, Inc. procedure is also described in Boudewyns et al., "Temperature controlled Radiofrequency Tissue Volume Reduction of the Soft Palate (Somnoplasty®) in the Treatment of Habitual Snoring: Results of a European Multicenter Trial", *Acta Otolaryngol*, Vol. 120 pp. 981–985 (2000) and Hukins et al., "Radiofrequency Tissue Volume Reduction of the Soft Palate in Simple Snoring", *Arch. Otolaryngol Head Neck Surg*, Vol. 126, pp. 602–606 (2000). Sclerosing therapy is also described in Brietzke et al., "Injection Snoreplasty: How to Treat Snoring Without All the Pain and Expense", *Otolaryngology—Head and Neck Surgery*, pp. 503–510 (May 2001).

SUMMARY OF THE INVENTION

According to a preferred embodiment of the present invention, a method is disclosed for treating snoring of a patient attributable at least in part to motion of a soft palate of the patient. The method includes identifying first and second locations disposed on right and left sides, respectively, of the soft palate and separated by an anterior-posterior midline extending centrally positioned on the palate. The first and second locations are linked across the midline by creating a linkage between the first and second locations and through the midline with the linkage having a stiffness greater than a stiffness of untreated tissue naturally residing between the locations.

DESCRIPTION OF THE PREFERRED EMBODIMENT

A. Incorporation By Reference of Earlier Publications

The teachings of commonly assigned U.S. Pat. No. 6,250,307 issued Jun. 26, 2001; International application PCT/US00/26616 (International Publication No. WO 01/23039 A1 published Apr. 5, 2001), International application PCT/US00/40830 (International Publication No. WO 01/19301 A1 published Mar. 22, 2001) and International application PCT/US01/24255 (International Publication No. WO 02/13732 published Feb. 2, 2002 are incorporated herein by reference.

B. Anatomical Background

For ease of understanding the present invention, the dynamics of snoring are explained with reference to FIGS. 1–4. The hard palate HP overlies the tongue T and forms the roof of the mouth M. The hard palate HP includes a bone support B and does not materially deform during breathing. The soft palate SP is soft and is made up of mucous membrane, fibrous and muscle tissue extending rearward from the hard palate HP. A leading end LE of the soft palate SP is anchored to the trailing end of the hard palate HP. A trailing end TE of the soft palate SP is unattached. Since the soft palate SP is not structurally supported by bone or hard cartilage, the soft palate SP droops down from the plane of the hard palate HP in an arcuate geometry of repose.

The pharyngeal airway passes air from the mouth M and the nasal passages N into the trachea TR. The portion of the pharyngeal airway defined between opposing surfaces of the upper surface of the soft palate SP and the wall of the throat is the nasopharynx NP.

Figures 1, 2:
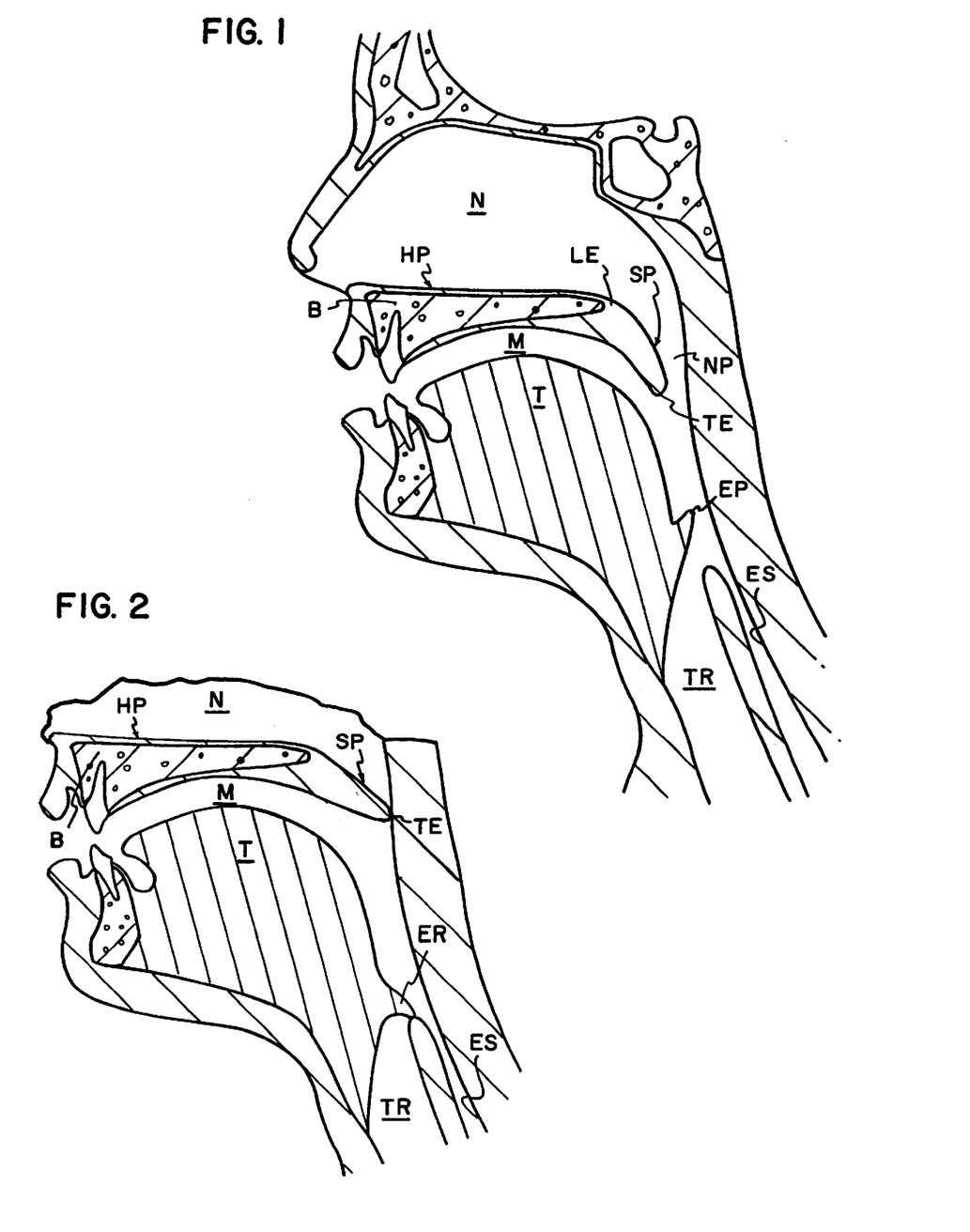
FIG. 1 is a side sectional view of a portion of a human head showing a soft palate in a relaxed state and in relation in adjacent anatomical features.
FIG. 2 is a portion of the view of FIG. 1 showing the soft palate in a flexed state.

During normal breathing, the soft palate SP is in the relaxed state shown in FIG. 1 with the nasopharynx NP unobstructed and with air free to flow into the trachea TR from both the mouth M and the nostrils N.

During swallowing, the soft palate SP flexes and extends (as shown in FIG. 2) to close the nasopharynx NP thereby preventing fluid flow from the mouth M to the nasal passages N. Simultaneously, the epiglottis EP closes the trachea TR so that food and drink pass only into the esophagus ES and not the trachea TR. The soft palate SP is a valve to prevent regurgitation of food into the nose N. The soft palate SP also regulates airflow through the nose N while talking. Since the soft palate SP performs such important functions, prior art techniques for surgically altering the soft palate SP can compromise these functions.

The majority of snoring is caused by the soft palate SP flapping back and forth. If breathing is solely through the nose N with the mouth closed, the trailing edge TE of the soft palate SP is sucked into the nasopharyngeal space NP obstructing the airway and subsequently falls opening the airway in a repeating cycle. When the mouth is open, air flows over the upper and lower surfaces of the soft palate SP causing the soft palate SP to flap up and down alternating in obstructing the oral and nasal passageways M, N. The snoring sound is generated by impulses caused by rapid obstruction and opening of airways. Huang, et al., state the airway passage opening and closing occurs 50 times per second during a snore. Huang, et al., utilize a spring-mass model (FIG. 5) to illustrate oscillation of the soft palate in response to airflow (where the soft palate is the ball B of mass depending by a spring S from a fixed anchor A).

Figure 3:
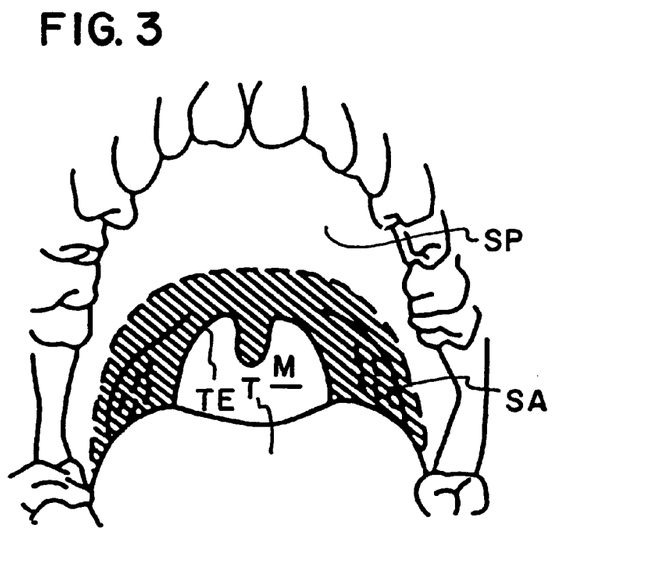
FIG. 3 is a front view of an interior of the mouth shown in FIG. 1 and showing an area to be ablated according to a first prior art surgical procedure.
Figure 4:
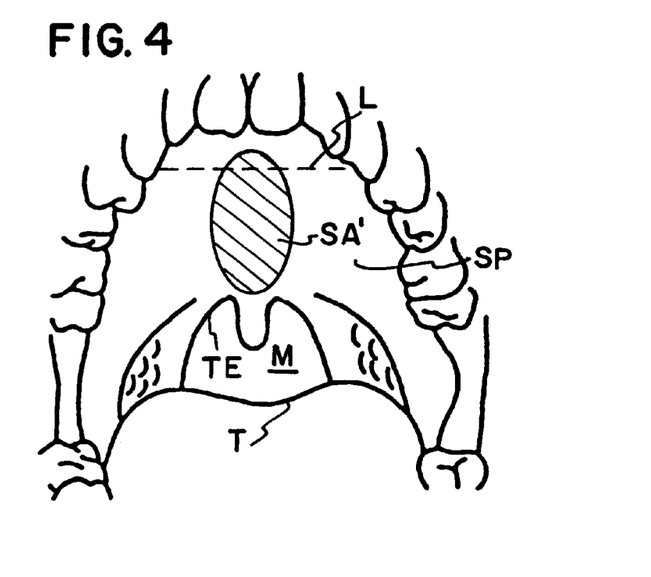
FIG. 4 is the view of FIG. 3 and showing an area to be scarred according to a second prior art surgical procedure.

Huang, et al., analogize the shortening of the soft palate SP in uvulopalatopharyngoplasty as effectively raising the critical airflow speed at which soft palate flutter will occur. The shaded area SA in FIG. 3 shows the area of the trailing end TE of the soft palate SP to be removed during this procedure. The alternative procedure proposed by Huang, et al., reduces the flexibility of the soft palate SP through surface scarring which is asserted as effecting the critical flow speed. The shaded area SA' in FIG. 4 shows the area to be scarred by this alternate procedure. In FIG. 4, dashed line L shows the demarcation between the soft and hard palates.

Figure 5:
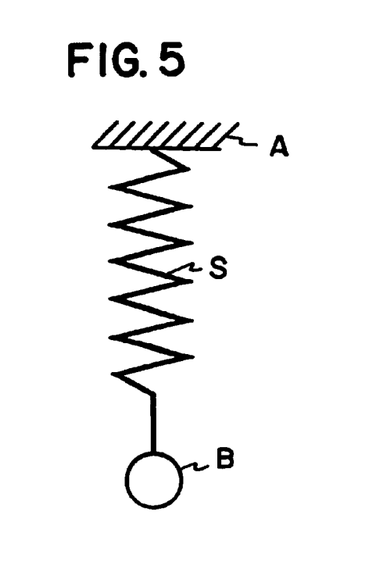
FIG. 5 is a schematic representation of a spring-mass system model of the soft palate.

Using the spring-mass model of FIG. 5 as a convenient model of the soft palate SP, the present invention is directed to a surgical implant into the soft palate SP to alter the elements of the model and thereby alter the dynamic response of the soft palate SP to airflow. The implant can alter the mass of the model (the ball B of FIG. 5), the spring constant of the spring S, the dampening of the spring S or any combination of these elements. Unlike the prior art surgical techniques, the implants that will be described are easy to insert in a small incision resulting in reduced patient discomfort and are not exposed to the interior of the mouth (such as the surface scarring of Huang, et al.) as a patient irritant. Also, as will be described, the degree of dynamic remodeling can be fine tuned avoiding the need for excessive anatomical modification and are reversible in the event of adverse consequences.

C. Representative Examples of Sub-Mucosal Techniques for Palatal Stiffening

FIGS. 6–15 illustrate examples of various designs and techniques of palatal stiffening with many of the examples described being shown in the incorporated by reference documents U.S. Pat. No. 6,250,307 issued Jun. 26, 2001; International application PCT/US00/26616 (International Publication No. WO 01/23039 A1 published Apr. 5, 2001), International application PCT/US00/40830 (International Publication No. WO 01/19301 A1 published Mar. 22, 2001) and International application PCT/US01/24255 (International Publication No. WO 02/13738 published Feb. 2, 2002.

1. Modular Implants

Figure 6:
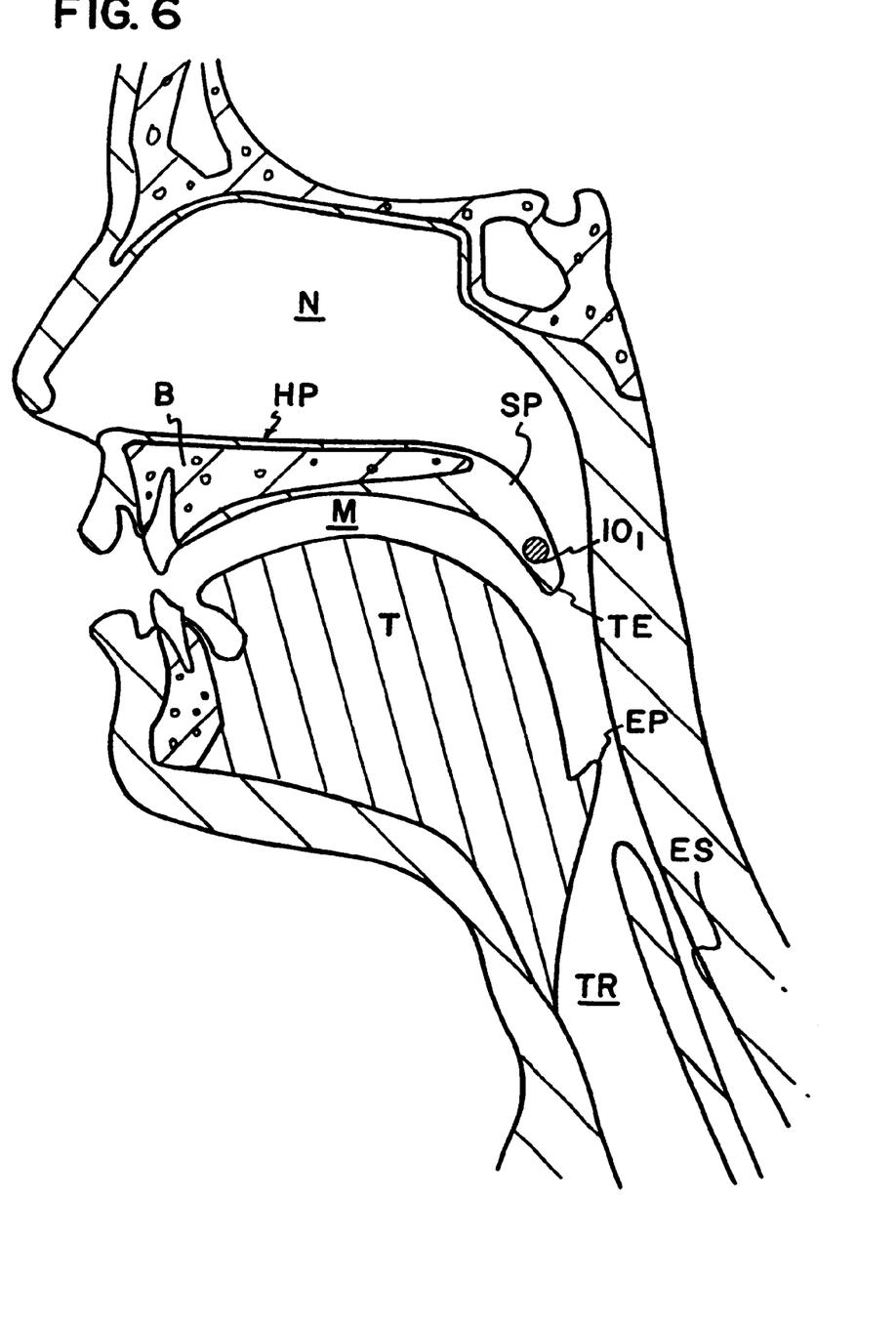
FIG. 6 is the view of FIG. 1 with the soft palate containing an implant according to a first embodiment of the present invention.
Figure 7:
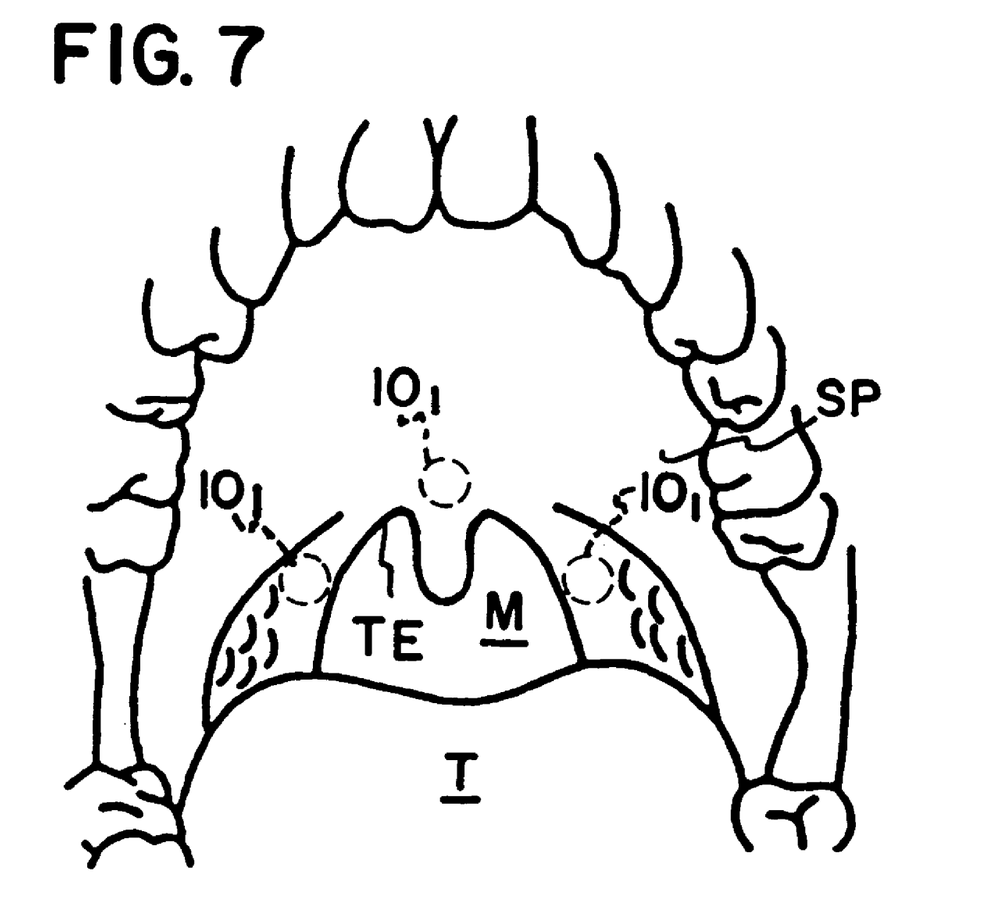
FIG. 7 is the view of FIG. 3 showing the embodiment of FIG. 6.

FIGS. 6–7 illustrate an example of one type of palatal implant $10_1$ as shown in U.S. Pat. No. 6,250,307. The implants $10_1$ are individual units of mass (in the form of implantable modular devices such as spheres or implants of other geometry) imbedded in the soft palate SP in close proximity to the trailing end TE.

As disclosed in U.S. Pat. No. 6,250,307, the spheres $10_1$ can be formed from a wide variety of biocompatible materials. Such materials may also include coatings, materials or surface treatments to induce a fibrotic response of palatal tissue following placement of the spheres $10_1$ in the palate SP.

2. Elongated Implants

Figure 8:
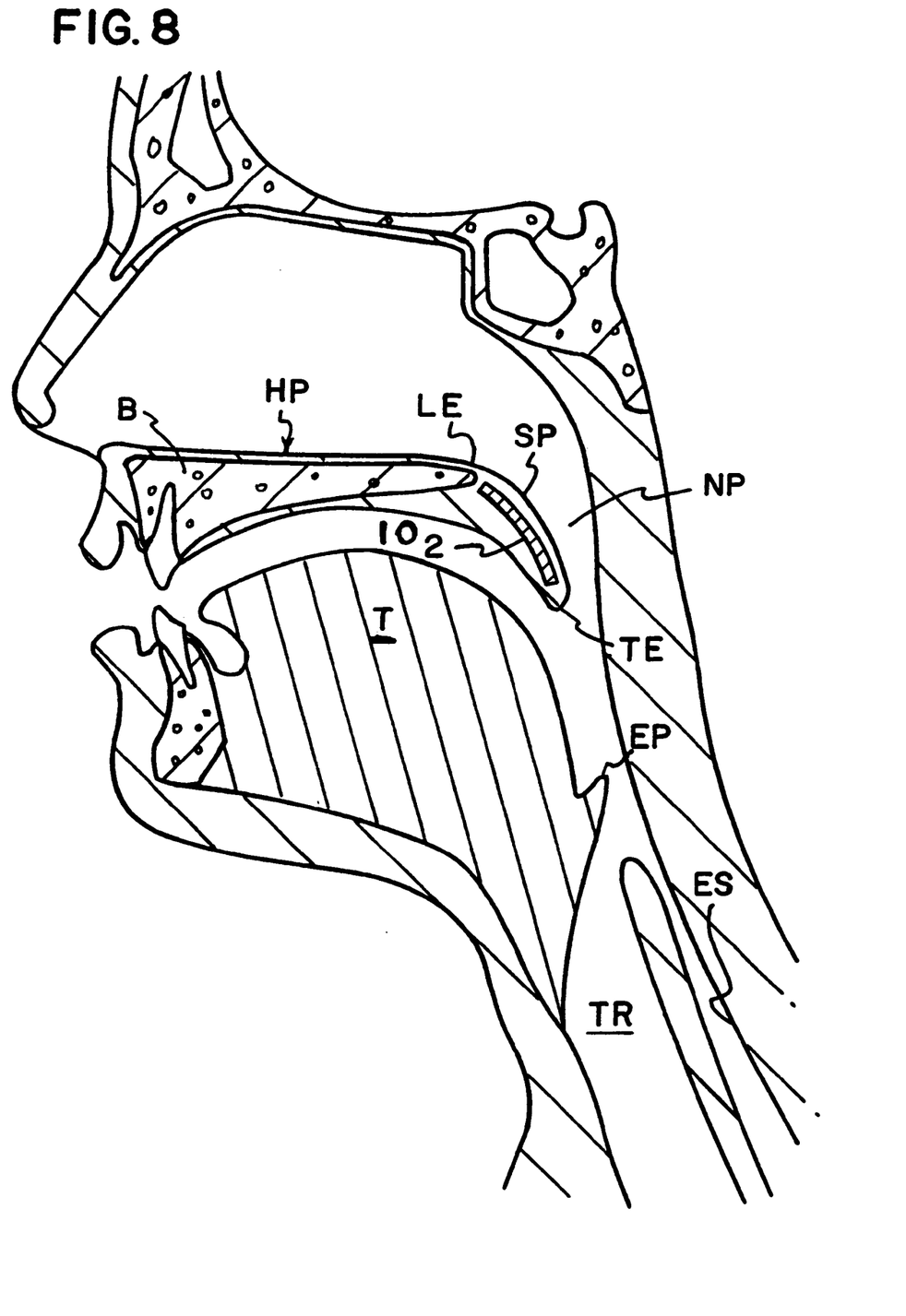
FIG. 8 is the view of FIG. 6 with the soft palate containing an implant according to a second embodiment of the present invention.
Figure 9:
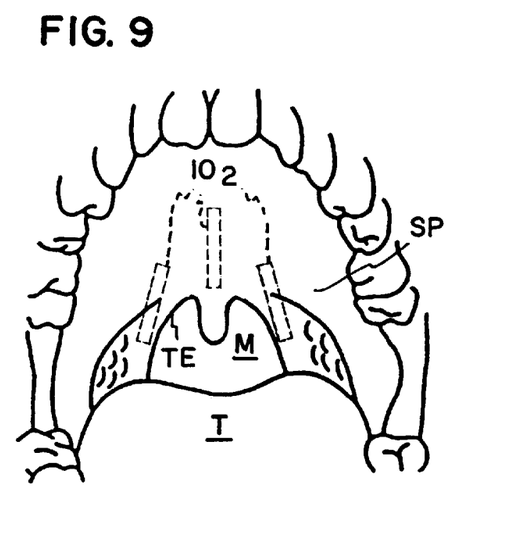
FIG. 9 is the view of FIG. 7 showing the embodiment of FIG. 8.

FIGS. 8–9 illustrate a second example of an implant $10_2$ as described more fully in U.S. Pat. No. 6,250,307. The implant $10_2$ is in the form of a flexible strip for placement in the soft palate SP. The use of the term "strip" herein is not intended to be limited to long, narrow implants but can also include plates or other geometries implanted to alter the dynamic model of the soft palate SP. In the embodiment of FIGS. 8–9, the strip $10_2$ is embedded in the soft palate SP with its longitudinal dimension extending from adjacent the hard palate HP toward the trailing end TE of the soft palate SP.

The strips $10_2$ may be any flexible, biocompatible material and may be radiopaque or radio-marked as well as MRI compatible. The strips can be a polymer strip, a polymer re-enforced with a rod, a hollow bladder member with an interior for receiving an injected polymer (all as taught in U.S. Pat. No. 6,250,307) or any other suitable material. The strips $10_2$ need not be elastic and having a material spring constant biasing them to their original shape. Such strips $10_2$ could simply be flexible, plastically deformable strips which are stiffer than the soft palate SP to reinforce the soft palate SP and assist the soft palate SP in resisting deflection due to airflow. Also, the strips $10_2$ may be formed of material more flexible than the tissue of the soft palate SP by selecting material (e.g., porous polyester) that induces a stiffening fibrotic response following implantation.

3. Braided Implants

Figure 10:
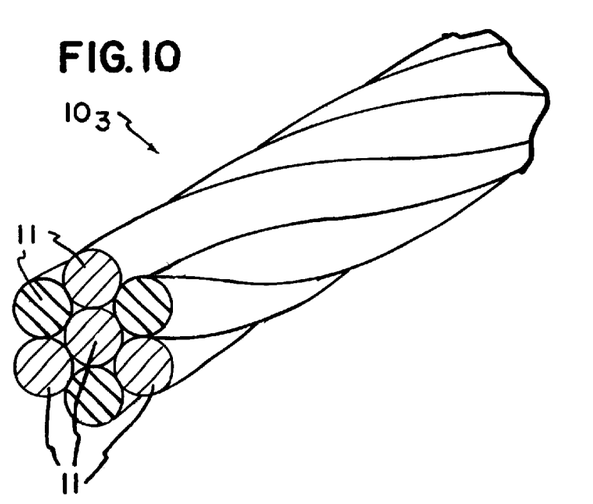
FIG. 10 is a perspective view of a braided implant.

As shown in FIG. 10, the implant $10_3$ may be a braid of biocompatible fibers 11. In the braid $10_3$, multiple types of fibers 11 may be used or all such fibers may be of a single type (e.g., polyester fibers). Also, selected ones or all of the fibers 11 may be so-called air-textured yarns to add fluffiness to the implant $10_3$ and promote tissue in-growth.

Figure 11:
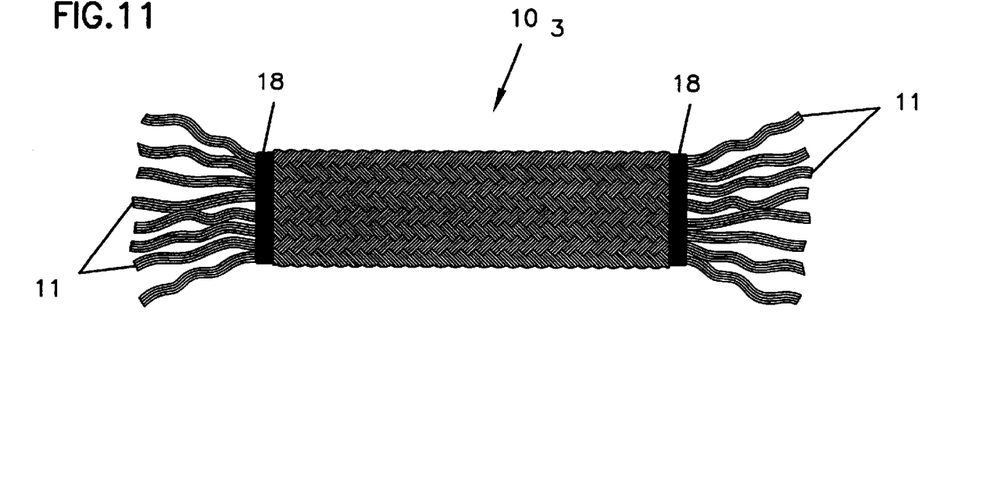
FIG. 11 is a side elevation view of a braided implant with end weld and frayed ends.

Braided fibers 11 may be heat-treated (as shown in FIG. 11) at the ends of the braid $10_3$ to prevent excessive fraying. Placing heat-treatment welds 18 at 1–2 mm from the ends of the braid $10_3$ permit limited fraying at the ends so the ends are soft and have enhanced tissue in-growth. Braids $10_3$ of the fore-going description are the subject matter of commonly assigned and co-pending U.S. patent application Ser. No. 09/814,471 filed Mar. 21, 2001. FIG. 11 is a copy (except for identifying numerals) of a FIG. from the '471 application.

4. Expandable Implant

Figure 12:
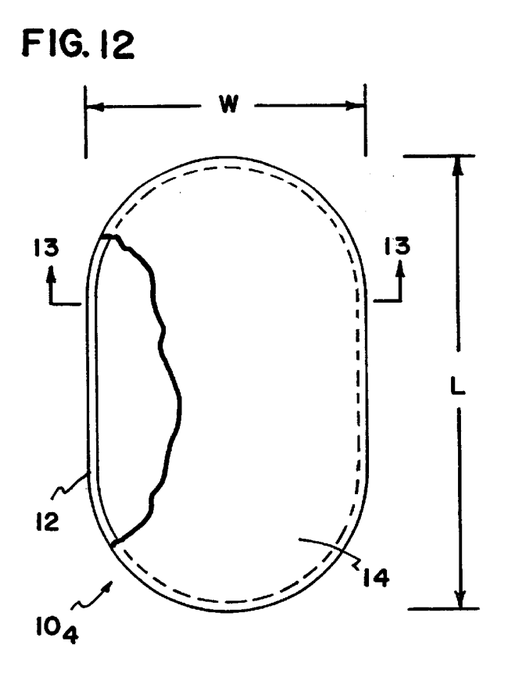
FIG. 12 is a top plan view, shown partially broken away, of a still further embodiment of the present invention.
Figure 13:
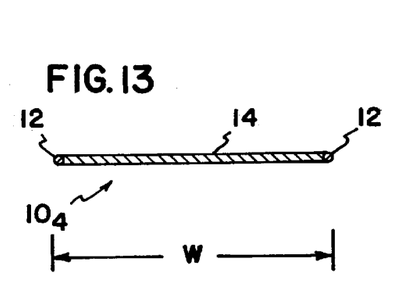
FIG. 13 is a view taken along line 13–13 in FIG. 12.
Figure 14:
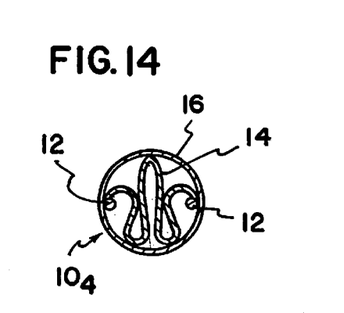
FIG. 14 is a cross-sectional view of the implant of FIG. 12 in a collapsed state in a needle for delivery.

As illustrated in FIGS. 12–14, the implant $10_4$ may also be an expandable frame 12 covered with a fibrosis-inducing material 14. For example, the implant $10_4$ may include a nitinol (or other suitable material) frame 12 with a polyester fabric coating 14 (FIGS. 12–14). Such a structure can be reduced to a collapsed state (FIG. 14), placed in a needle 16 and inserted through a small wound for later expansion. Examples of all of the foregoing (other than FIG. 11 taken from the afore-mentioned '471 application) are more fully described in the afore-mentioned International Publication WO 01/19301.

5. Sheet Implant

Figure 15:
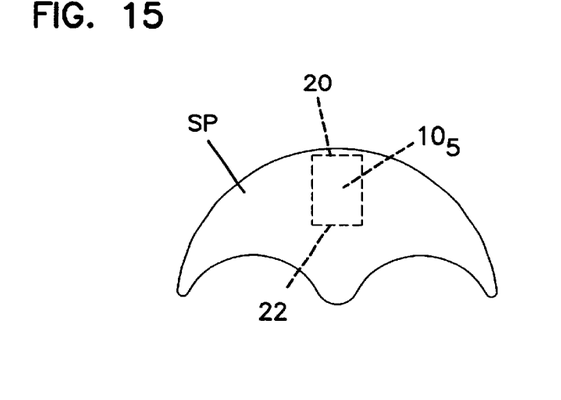
FIG. 15 is a frontal view of a soft palate and showing an implant of sheet material in phantom lines in place in the soft palate.

Shown in FIG. 15, the implant $10_5$ may also be a flexible flat sheet material having openings (such as pores or fibers defining interstitial spaces) for tissue in-growth. An example of a porous material is expanded PTFE. Such fibrous materials may be woven or knit materials such as polyester felt or velour. By way of illustration, the sheet may have a width of 5–10 mm, thickness of 1.5 mm (measured between generally flat upper and lower surfaces) and length (measured between proximal and distal edges 20, 22) of 20 mm for the implant $10_5$ to be inserted into the soft palate SP.

In FIG. 15, the implant $10_5$ is shown lying flat in the soft palate SP with the longitudinal axis of the implant $10_5$ aligned with the anterior-posterior axis of the palate SP and with the width of the implant $10_5$ aligned with the lateral axis of the palate SP. The flat lower surface of the implant $10_5$ is generally parallel to the lower surface of the soft palate SP. FIG. 15 is a copy (except for identifying numerals) of a FIG. appearing in commonly assigned and copending patent application Ser. Nos. 09/814,460 and 09/815,154 both filed Mar. 21, 2001. Those applications also disclose tools for placing of the implant $10_5$ and describe placement in a proximal two-thirds of the soft palate.

6. Particulate Implants

Figure 16:
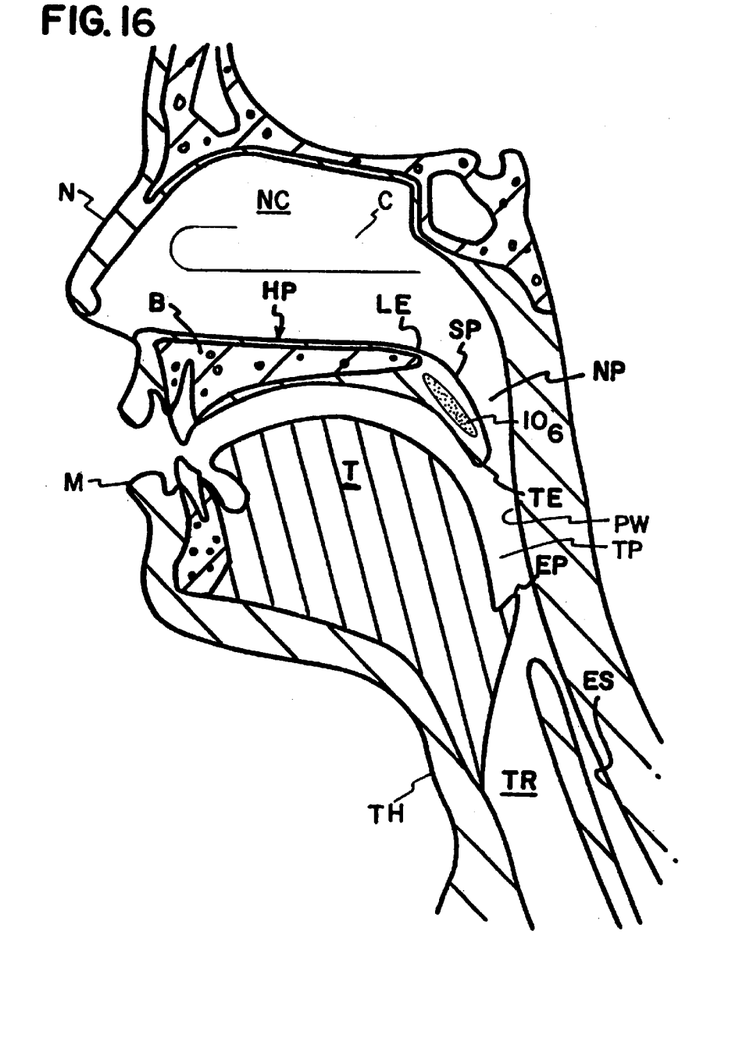
FIG. 16 is the view of FIG. 6 with the implant in the form of a bolus of particulate material.

FIG. 16 shows an implant $10_6$ as a bolus of particulate matter. An example of such particulate matter would be micro-beads. Such microbeads are described in U.S. Pat. Nos. 5,792,478 and 5,421,406. These patents teach carbon-coated metallic or ceramic particles having cross-sectional dimensions of between 100 and 1,000 microns. The particles are carried in a fluid or gel. These patents state that upon insertion into body tissue, the particles do not migrate significantly and, apparently due to fibrotic response, the tissue into which the particles are injected stiffens. Use of micro-beads in palatal stiffening is shown in commonly assigned and copending U.S. patent application Ser. No. 09/636,803 filed Aug. 10, 2000 (International patent application PCT/US01/24255).

7. Radiofrequency Ablation

In addition to the foregoing, submucosal palatal stiffening includes radio-frequency (RF) ablation of the tissue of the palate by placement of a needle-tip in the soft palate. The needle-tip includes an RF energy emitter which ablates tissue and forms a scar. RF ablation of the soft palate is described in Kasey et al., "Radiofrequency Volumetric Reduction of the Palate: An Extended Follow-Up Study", *Otolaryngology—Head and Neck Surgery*, Vol. 122, No. 3, pp. 410–414 (Mar. 2000).

Such RF ablation is not an implant and does not provide a permanent scar. Therefore, any resulting benefits are generally temporary.

8. Sclerosing Agents

The use of sclerosing agents to treat the soft palate is described in LaFrentz et al., "Palatal Stiffening Techniques for Snoring in a Novel Canine Model", *Abstracts of the Twenty-Second Annual MidWinter Meeting of the Association for Research in Otolaryngology*, Abstract NO. 499, Vol. 22, pp. 125–126 (Feb. 13–18, 1999). Like RF ablation, sclerosing treatment is not an implant and does not provide a permanent scar. Therefore, any resulting benefits are generally temporary. Also, the sclerosing is difficult to control.

D. Method of the Present Invention

The method of the present invention is directed to the use of palatal stiffening techniques (e.g., any of the foregoing) used to create a lateral stiffening of the soft palate. The method includes identifying first and second locations disposed on right and left sides, respectively, of the soft palate and separated by an anterior-posterior midline extending centrally positioned on the palate. The first and second locations are linked across the midline by creating a linkage between the first and second locations and through the midline. The linkage has a stiffness greater than a stiffness of untreated tissue naturally residing between the locations.

Figure 17:
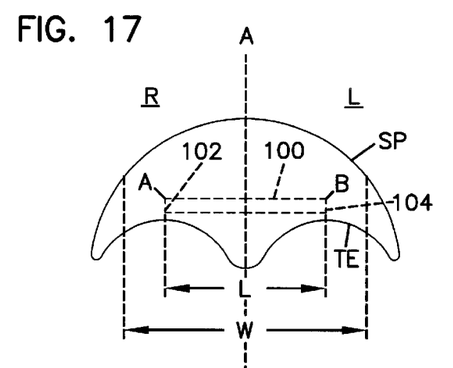
FIG. 17 is a frontal view of a soft palate with a strip implant placed for lateral stiffening according to the present invention.

The method of the present invention is illustrated in FIG. 17 showing a soft palate SP with an anterior-posterior midline AP separating the soft palate SP into left and right sides L, R ("left" and "right" being labeled from the patient's perspective).

Two locations A, B are labeled on the soft palate on the right R and left L sides, respectively. An implant 100 is shown imbedded in the soft palate with ends 102, 104 of the implant residing at locations A, B. Preferably, the implant 100 is a strip of material having a length (distance between the implant ends 102, 104) greater than a transverse dimension. An example of such an implant 100 is any of the foregoing strip implants or braids. Also, it is presently preferred that the implant 100 include structure to facilitate tissue in-growth and fibrotic response. An example is a braid of polyester fibers including a mixture of air-textured yarns.

With the structure thus described, the implant 100 links the first and second locations A, B across the midline AP. The linkage (which includes the fibrotic response to the implant together with any material stiffness of the implant) has a stiffness greater than a stiffness of the untreated tissue between the locations A, B.

FIG. 9 illustrates a placement of strip implants in the afore-said U.S. Pat. No. 6,250,307. In the embodiment there disclosed, the implants $10_2$ are placed with longitudinal axes generally parallel to the anterior-posterior axis of the soft palate. Such placement may conveniently be referred to as "longitudinal" stiffening. The present invention is directed to what may conveniently be described as "lateral stiffening". It is presently believed lateral stiffening provides a significant increase in the stiffness of the soft palate for any given size, structure or degree of fibrosis of palatal implant.

In the embodiment of FIG. 17, it is presently believed that the length of the implant 100 (distance between ends 102, 104) be at least 25% (and more preferably at least 50%) of the width W of the soft palate SP at the location of the implant 100. It is preferred the implant 100 be placed in the distal 75% (and more preferably the distal 50%) of the soft palate SP. It is presently anticipated that placement as close as possible to the soft palate trailing edge TE is most desirable.

Figure 18:
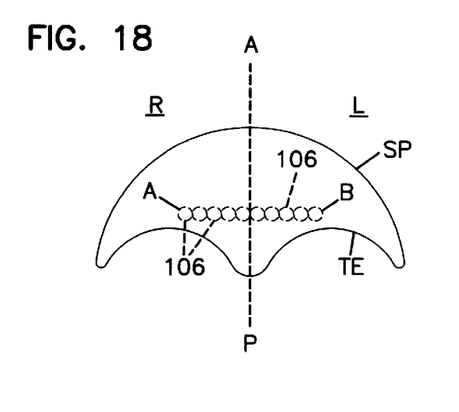
FIG. 18 is the view of FIG. 17 with an alternative formation of the lateral stiffening.

FIG. 18 illustrates a soft palate SP treated with lateral stiffening using a stiffening mechanism other than the strip implant 100 shown in FIG. 17. In FIG. 18, a linear array of multiple spheres 106 of fibrosis are formed in the soft palate SP with the fibrotic scar of adjacent spheres 106 overlapping to link the locations A, B. The spheres 106 may be formed by spherical implants (such as implants $10_1$ in FIGS. 6–7) or may be formed by placing multiple RF ablation treatments between the locations A, B. Alternatively, a single RF ablation treatment can be formed in a linear path between locations A, B. RF ablation treatments create a scar which shrinks over time. Preferably, such shrinkage is taken into account when linking locations A, B. A still further embodiment is a controlled linear treatment or injection of a sclerosing agent into the soft palate between locations A, B.

Figure 19:
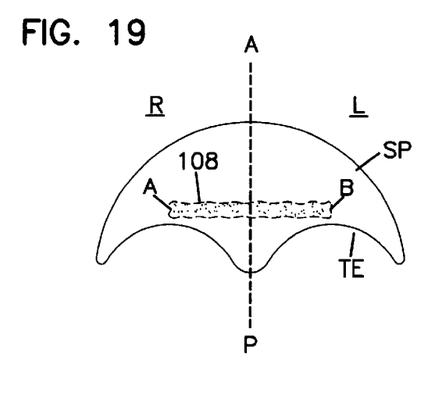
FIG. 19 is the view of FIG. 17 with a further alternative formation of the lateral stiffening.

FIG. 19 illustrates a soft palate SP treated with lateral stiffening using a still further mechanism other than those described above. In FIG. 19, a polymer 108 (e.g., silicone) is injected in a linear path between locations A, B. Alternatively, microbeads can be injected in the linear path between locations A, B.

Figure 20:
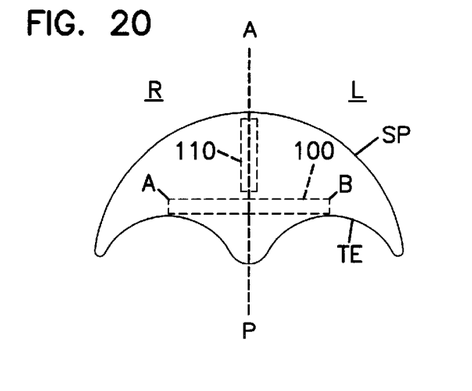
FIG. 20 is the view of FIG. 17 with an additional implant for longitudinal stiffening.

FIG. 20 illustrates a modification of the embodiment of FIG. 17 in which an additional strip implant 110 is placed with a longitudinal axis parallel to the midline AP. The longitudinal implant 110 provides longitudinal stiffness as well as minimizing any longitudinal stretching of the soft palate SP which might otherwise occur over time.

From the foregoing detailed description, it has been shown how the present invention is attained in a preferred embodiment. Modifications and equivalents such as those which may be apparent to one of skill in the art are intended to be included in the scope of the appended claims.

What is claimed is:

1. A method of treating snoring attributed at least in part to movement of a soft palate of a patient in response to air flow, the method comprising:

identifying first and second locations disposed on right and left sides, respectively of the soft palate and separated by an anterior-posterior midline extending centrally positioned on said palate;

linking said first and second locations across said midline;

said linking including creating a linkage between said first and second locations and through said midline with said linkage having a stiffness greater than a stiffness of untreated tissue naturally residing between said locations.

2. A method according to claim 1 wherein said linkage is submucosal.

3. A method according to claim 2 wherein said linkage is created at least in part by forming a scar tissue in said soft palate between said first and second locations.

4. A method according to claim 3 wherein said scar tissue is formed by radio-frequency ablation.

5. A method according to claim 2 wherein said linkage is created at least in part by placing an implant in said soft palate with said implant having a longitudinal dimension extending between said first and second locations with any natural stiffness of said implant and any fibrotic response to said implant creating said stiffness of said linkage.

6. A method according to claim 5 wherein said implant is a non-dissolving, biocompatible material.

7. A method according to claim 2 wherein said locations are spaced-apart for said linkage to have a length equal to greater than one-third of a width of the soft palate at the position of said implant.

8. A method according to claim 2 wherein said locations are positioned near a trailing edge of said soft palate.

9. A method according to claim 8 wherein said locations are positioned in a distal one-third of the soft palate.

10. A method according to claim 2 wherein said linkage is created for said locations to be positioned for a straight line extending between said locations to be generally orthogonal to said midline.

11. A method according to claim 3 wherein said scar tissue is formed by injecting a sclerosing agent into said soft palate between said locations.

12. A method according to claim 3 wherein said scar tissue is formed by injecting microbeads into said soft palate between said locations.

13. A method according to claim 3 wherein said scar tissue is formed by injecting a stiffening polymer into said soft palate between said locations.

14. A method according to claim 13 wherein said polymer is silicone.

15. A method according to claim 1 wherein the linkage has a length between the first and second locations greater than a dimension transverse to the length.

16. A method according to claim 1 further including creating a longitudinal linkage in said soft palate and extending parallel to said midline.

17. A method according to claim 1 wherein said linkage has a length sufficient for said linkage to extend at least 25% of a width of said soft palate.

18. A method according to claim 17 wherein said linkage has a length sufficient for said linkage to extend at least 50% of a width of said soft palate.

19. A method according to claim 1 wherein the linkage is placed in the distal 75% of the soft palate.

20. A method according to claim 19 wherein the linkage is placed in the distal 50% of the soft palate.

\* \* \* \* \*

UNITED STATES PATENT AND TRADEMARK OFFICE
CERTIFICATE OF CORRECTION

PATENT NO.    : 6,502,574 B2                                              Page 1 of 1
DATED         : January 7, 2003
INVENTOR(S)   : Stevens et al.

It is certified that error appears in the above-identified patent and that said Letters Patent is hereby corrected as shown below:

<u>Title page,</u>
Item [63], Related U.S. Application Data, "039, filed on Feb. 25, 2000, which is a continuation-in-part" should read -- 039, filed on Feb. 25, 2000, which are continuations-in-part --

Signed and Sealed this

Fourth Day of May, 2004

JON W. DUDAS
*Acting Director of the United States Patent and Trademark Office*